United States Patent
Coleman

(10) Patent No.: US 7,615,015 B2
(45) Date of Patent: *Nov. 10, 2009

(54) FOCUSED ULTRASOUND ABLATION DEVICES HAVING SELECTIVELY ACTUATABLE EMITTING ELEMENTS AND METHODS OF USING THE SAME

(75) Inventor: R. Glen Coleman, Jacksonville, FL (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/600,871

(22) Filed: Jun. 20, 2003

(65) Prior Publication Data

US 2004/0015106 A1    Jan. 22, 2004

Related U.S. Application Data

(63) Continuation of application No. 09/487,710, filed on Jan. 19, 2000, now Pat. No. 6,692,450.

(51) Int. Cl.
*A61H 1/00* (2006.01)
*A61H 1/02* (2006.01)
*A61H 5/00* (2006.01)

(52) U.S. Cl. ................... 601/3; 606/27; 601/2
(58) Field of Classification Search .......... 600/439, 600/471, 472; 601/1–4; 606/27–31
See application file for complete search history.

(56) References Cited

U.S. PATENT DOCUMENTS

| | | |
|---|---|---|
| 3,736,936 A | 6/1973 | Basiulis et al. |
| 3,807,403 A | 4/1974 | Stumpf et al. |
| 3,823,575 A | 7/1974 | Parel |
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |

(Continued)

FOREIGN PATENT DOCUMENTS

EP    1 095 627    5/2001

(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner*—Long V Le
*Assistant Examiner*—Jacqueline Cheng
(74) *Attorney, Agent, or Firm*—Mike Jaro; Jeffrey J. Hohenshell

(57) ABSTRACT

A focused ultrasound ablation device and method includes an ultrasound emitting member having a plurality of individual ultrasound emitting elements arranged in an array. The ultrasound emitting elements are actuatable to emit ultrasound energy and focus the emitted ultrasound energy a predetermined distance from the ultrasound emitting member such that the ultrasound energy is focused within anatomical tissue adjacent which the ultrasound emitting member is positioned. The anatomical tissue is heated by the ultrasound energy focused therein to form an internal lesion within the tissue. The ultrasound emitting elements are selectively, independently actuatable, allowing selected ones of the ultrasound emitting elements to be actuated to emit ultrasound energy to obtain a lesion of desired or selected size and/or surface configuration in the tissue of a particular patient.

95 Claims, 2 Drawing Sheets

U.S. PATENT DOCUMENTS

| | | | |
|---|---|---|---|
| 3,913,581 A | 10/1975 | Ritson et al. | |
| 3,924,628 A | 12/1975 | Droegemueller et al. | |
| 3,990,452 A | 11/1976 | Murry et al. | 128/305 |
| 4,018,227 A | 4/1977 | Wallach | |
| 4,022,215 A | 5/1977 | Benson | |
| 4,061,135 A | 12/1977 | Widran et al. | |
| 4,063,560 A | 12/1977 | Thomas et al. | |
| 4,072,152 A | 2/1978 | Linehan | |
| 4,082,096 A | 4/1978 | Benson | |
| 4,207,897 A | 6/1980 | Lloyd et al. | |
| 4,248,224 A | 2/1981 | Jones | |
| 4,275,734 A | 6/1981 | Mitchiner | |
| 4,278,090 A | 7/1981 | van Gerven | |
| 4,377,168 A | 3/1983 | Rzasa et al. | |
| 4,508,122 A | 4/1985 | Gardineer et al. | 128/660 |
| 4,519,389 A | 5/1985 | Gudkin et al. | |
| 4,562,900 A * | 1/1986 | Anderson et al. | 181/176 |
| 4,598,698 A | 7/1986 | Siegmund | |
| 4,601,290 A | 7/1986 | Effron et al. | |
| 4,646,756 A * | 3/1987 | Watmough et al. | 607/154 |
| 4,658,828 A | 4/1987 | Dory | 128/660 |
| 4,664,110 A | 5/1987 | Schanzlin | |
| 4,736,749 A | 4/1988 | Lundback | |
| 4,779,611 A | 10/1988 | Grooters et al. | |
| 4,802,475 A | 2/1989 | Weshahy | |
| 4,807,633 A | 2/1989 | Fry | 128/660.02 |
| 4,815,470 A | 3/1989 | Curtis et al. | |
| 4,858,613 A | 8/1989 | Fry et al. | 128/660.03 |
| 4,872,346 A | 10/1989 | Kelly-Fry et al. | |
| 4,916,922 A | 4/1990 | Mullens | |
| 4,917,095 A | 4/1990 | Fry et al. | |
| 4,917,096 A | 4/1990 | Englehart et al. | 128/660.1 |
| 4,936,281 A | 6/1990 | Stasz | |
| 4,946,460 A | 8/1990 | Merry et al. | |
| 4,951,653 A | 8/1990 | Fry et al. | 128/24 |
| 4,955,365 A | 9/1990 | Fry et al. | 128/24 |
| 5,010,886 A | 4/1991 | Passafaro et al. | |
| RE33,590 E | 5/1991 | Dory | 128/660.03 |
| 5,013,312 A | 5/1991 | Parins et al. | |
| 5,029,574 A | 7/1991 | Shimamura et al. | |
| 5,033,456 A | 7/1991 | Pell et al. | 128/24 |
| 5,036,855 A | 8/1991 | Fry et al. | 128/660.03 |
| 5,044,165 A | 9/1991 | Linner et al. | |
| 5,054,470 A | 10/1991 | Fry et al. | 128/24 |
| 5,065,761 A | 11/1991 | Pell | 128/660.03 |
| 5,078,713 A | 1/1992 | Varney | |
| 5,080,101 A | 1/1992 | Dory | 128/660.03 |
| 5,080,102 A | 1/1992 | Dory | 128/660.03 |
| 5,080,660 A | 1/1992 | Buelina | |
| 5,100,388 A | 3/1992 | Behl et al. | |
| 5,108,390 A | 4/1992 | Potocky et al. | |
| 5,117,832 A | 6/1992 | Sanghvi et al. | 128/662.03 |
| 5,134,988 A | 8/1992 | Pell et al. | 128/24 |
| 5,143,074 A | 9/1992 | Dory | 128/660.03 |
| 5,147,355 A | 9/1992 | Friedman et al. | |
| 5,150,711 A | 9/1992 | Dory | 128/660.03 |
| 5,150,712 A | 9/1992 | Dory | 128/660.03 |
| 5,158,070 A | 10/1992 | Dory | 128/240 |
| 5,178,133 A | 1/1993 | Pena | |
| 5,207,674 A | 5/1993 | Hamilton | |
| 5,217,860 A | 6/1993 | Fahy et al. | |
| 5,222,501 A | 6/1993 | Ideker et al. | 128/660.03 |
| 5,224,943 A | 7/1993 | Goddard | |
| 5,228,923 A | 7/1993 | Hed | |
| 5,231,995 A | 8/1993 | Desai | |
| 5,232,516 A | 8/1993 | Hed | |
| 5,247,935 A | 9/1993 | Cline et al. | 128/653.2 |
| 5,254,116 A | 10/1993 | Baust et al. | |
| 5,263,493 A | 11/1993 | Avitall | |
| 5,267,954 A | 12/1993 | Nita | 604/22 |
| 5,269,291 A | 12/1993 | Carter | 128/24 |
| 5,269,297 A | 12/1993 | Weng et al. | 128/24 |
| 5,275,595 A | 1/1994 | Dobak, III | |
| 5,277,201 A | 1/1994 | Stern | |
| 5,281,213 A | 1/1994 | Milder et al. | |
| 5,281,215 A | 1/1994 | Milder | |
| 5,295,484 A | 3/1994 | Marcus et al. | 128/660.03 |
| 5,304,115 A | 4/1994 | Pflueger et al. | 604/22 |
| 5,309,896 A | 5/1994 | Moll et al. | |
| 5,312,328 A | 5/1994 | Nita et al. | 604/22 |
| 5,314,466 A | 5/1994 | Stern et al. | |
| 5,316,000 A | 5/1994 | Chapelon et al. | |
| 5,317,878 A | 6/1994 | Bradshaw et al. | |
| 5,318,014 A | 6/1994 | Carter | 601/2 |
| 5,318,525 A | 6/1994 | West et al. | |
| 5,322,520 A | 6/1994 | Milder | |
| 5,323,781 A | 6/1994 | Ideker et al. | |
| 5,324,255 A | 6/1994 | Passafaro et al. | |
| 5,324,284 A | 6/1994 | Imran | |
| 5,324,286 A | 6/1994 | Fowler | |
| 5,334,181 A | 8/1994 | Rubinsky et al. | |
| 5,334,193 A | 8/1994 | Nardella | |
| 5,342,292 A | 8/1994 | Nita et al. | 604/22 |
| 5,348,554 A | 9/1994 | Imran et al. | |
| 5,353,783 A | 10/1994 | Nakao et al. | |
| 5,354,258 A | 10/1994 | Dory | 601/3 |
| 5,361,752 A | 11/1994 | Moll et al. | |
| 5,380,274 A | 1/1995 | Nita | 604/22 |
| 5,385,148 A | 1/1995 | Lesh et al. | |
| 5,391,197 A | 2/1995 | Burdette et al. | 607/97 |
| 5,396,887 A | 3/1995 | Imran | |
| 5,397,301 A | 3/1995 | Pflueger et al. | 604/22 |
| 5,397,304 A | 3/1995 | Truckai | |
| 5,400,770 A | 3/1995 | Nakao et al. | |
| 5,400,783 A | 3/1995 | Pomeranz et al. | |
| 5,402,792 A | 4/1995 | Kimura | |
| 5,403,309 A | 4/1995 | Coleman et al. | |
| 5,403,311 A | 4/1995 | Abele et al. | |
| 5,405,376 A | 4/1995 | Mulier et al. | |
| 5,409,002 A | 4/1995 | Pell | 128/653.1 |
| 5,409,483 A | 4/1995 | Campbell et al. | |
| 5,413,550 A * | 5/1995 | Castel | 601/2 |
| 5,417,672 A | 5/1995 | Nita et al. | 604/283 |
| 5,423,807 A | 6/1995 | Milder | |
| 5,423,811 A | 6/1995 | Imran et al. | |
| 5,423,812 A | 6/1995 | Ellman et al. | 606/45 |
| 5,427,119 A | 6/1995 | Swartz et al. | |
| 5,431,621 A | 7/1995 | Dory | 601/2 |
| 5,431,649 A | 7/1995 | Mulier et al. | |
| 5,431,663 A | 7/1995 | Carter | 606/128 |
| 5,433,708 A | 7/1995 | Nichols et al. | |
| 5,435,308 A | 7/1995 | Gallup et al. | |
| 5,437,651 A | 8/1995 | Todd et al. | |
| 5,437,664 A | 8/1995 | Cohen et al. | |
| 5,441,499 A | 8/1995 | Fritzsch | |
| 5,443,463 A | 8/1995 | Stern et al. | |
| 5,443,470 A | 8/1995 | Stern et al. | |
| 5,447,509 A | 9/1995 | Mills et al. | 606/1 |
| 5,448,994 A * | 9/1995 | Iinuma | 600/439 |
| 5,450,843 A | 9/1995 | Moll et al. | |
| 5,452,582 A | 9/1995 | Longsworth | |
| 5,456,662 A | 10/1995 | Edwards et al. | 604/22 |
| 5,462,545 A | 10/1995 | Wang et al. | |
| 5,465,717 A | 11/1995 | Imran et al. | |
| 5,469,853 A | 11/1995 | Law et al. | |
| 5,472,876 A | 12/1995 | Fahy | |
| 5,474,530 A | 12/1995 | Passafaro et al. | 604/22 |
| 5,478,309 A | 12/1995 | Sweezer et al. | |
| 5,478,330 A | 12/1995 | Imran et al. | |
| 5,486,193 A | 1/1996 | Bourne et al. | |
| 5,487,385 A | 1/1996 | Avitall | |
| 5,487,757 A | 1/1996 | Truckai et al. | |
| 5,492,126 A | 2/1996 | Hennige et al. | 128/660.03 |
| 5,496,312 A | 3/1996 | Klicek | |

| | | | | | |
|---|---|---|---|---|---|
| 5,497,774 A | 3/1996 | Swartz et al. | 5,738,114 A | 4/1998 | Edwards ...................... 128/898 |
| 5,498,248 A | 3/1996 | Milder | 5,743,870 A | 4/1998 | Edwards ........................ 604/22 |
| 5,500,012 A | 3/1996 | Brucker et al. | 5,743,904 A | 4/1998 | Edwards ........................ 606/32 |
| 5,501,655 A | 3/1996 | Rolt et al. ........................ 601/3 | 5,746,224 A | 5/1998 | Edwards ...................... 128/898 |
| 5,505,730 A | 4/1996 | Edwards | 5,755,760 A | 5/1998 | Maguire et al. |
| 5,514,131 A | 5/1996 | Edwards et al. ................ 606/45 | 5,762,066 A | 6/1998 | Law et al. ............... 128/660.03 |
| 5,516,505 A | 5/1996 | McDow | 5,769,846 A | 6/1998 | Edwards et al. |
| 5,520,188 A | 5/1996 | Hennige et al. ......... 128/662.03 | 5,782,828 A | 7/1998 | Chen et al. |
| 5,520,682 A | 5/1996 | Baust et al. | 5,785,706 A | 7/1998 | Bednarek |
| 5,522,870 A | 6/1996 | Ben-Zion | 5,788,636 A | 8/1998 | Curley |
| 5,536,267 A | 7/1996 | Edwards et al. | 5,792,140 A | 8/1998 | Tu et al. |
| 5,542,917 A | 8/1996 | Nita et al. ...................... 604/22 | 5,797,960 A | 8/1998 | Stevens et al. ............... 606/213 |
| 5,545,195 A | 8/1996 | Lennox et al. | 5,800,379 A | 9/1998 | Edwards ........................ 604/22 |
| 5,545,200 A | 8/1996 | West et al. | 5,800,428 A | 9/1998 | Nelson et al. |
| 5,549,661 A | 8/1996 | Kordis et al. | 5,800,429 A | 9/1998 | Edwards ........................ 606/41 |
| 5,555,883 A | 9/1996 | Avitall | 5,800,482 A | 9/1998 | Pomeranz et al. ........... 607/101 |
| 5,558,671 A | 9/1996 | Yates | 5,807,308 A | 9/1998 | Edwards ........................ 604/22 |
| 5,560,362 A | 10/1996 | Sliwa, Jr. et al. | 5,810,802 A | 9/1998 | Panescu et al. |
| 5,562,720 A | 10/1996 | Stern et al. | 5,817,049 A | 10/1998 | Edwards ........................ 604/22 |
| 5,569,241 A | 10/1996 | Edwards | 5,823,197 A | 10/1998 | Edwards ...................... 128/898 |
| 5,571,088 A | 11/1996 | Lennox et al. | 5,827,216 A | 10/1998 | Igo et al. |
| 5,573,532 A | 11/1996 | Chang et al. | 5,827,277 A | 10/1998 | Edwards ........................ 606/41 |
| 5,575,788 A | 11/1996 | Baker et al. | 5,836,947 A | 11/1998 | Fleischman et al. |
| 5,575,810 A | 11/1996 | Swanson et al. | 5,840,030 A | 11/1998 | Ferek-Petric et al. |
| 5,578,007 A | 11/1996 | Imran | 5,843,077 A | 12/1998 | Edwards ........................ 606/41 |
| 5,582,609 A | 12/1996 | Swanson et al. | 5,844,349 A | 12/1998 | Oakley et al. |
| 5,588,432 A | 12/1996 | Crowley | 5,846,187 A | 12/1998 | Wells et al. |
| 5,590,657 A | 1/1997 | Cain et al. ............. 128/660.03 | 5,846,191 A | 12/1998 | Wells et al. |
| 5,595,183 A | 1/1997 | Swanson et al. | 5,849,028 A | 12/1998 | Chen |
| 5,607,462 A | 3/1997 | Imran | 5,871,523 A | 2/1999 | Fleischman et al. |
| 5,617,854 A | 4/1997 | Munsif | 5,871,524 A | 2/1999 | Knowlton ...................... 607/101 |
| 5,620,479 A | 4/1997 | Diederich ...................... 607/97 | 5,871,525 A | 2/1999 | Edwards et al. |
| 5,624,439 A | 4/1997 | Edwards et al. ................ 606/45 | 5,873,845 A | 2/1999 | Cline et al. ....................... 601/3 |
| 5,630,837 A | 5/1997 | Crowley | 5,873,902 A | 2/1999 | Sanghvi et al. ................ 607/96 |
| 5,637,090 A | 6/1997 | McGee et al. | 5,876,399 A | 3/1999 | Chia et al. |
| 5,643,197 A | 7/1997 | Brucker et al. | 5,879,295 A | 3/1999 | Li et al. |
| 5,656,029 A | 8/1997 | Imran et al. | 5,879,296 A | 3/1999 | Ockuly et al. |
| 5,658,278 A | 8/1997 | Imran et al. | 5,879,349 A | 3/1999 | Edwards ........................ 606/45 |
| 5,671,747 A | 9/1997 | Connor | 5,881,732 A | 3/1999 | Sung et al. |
| 5,676,662 A | 10/1997 | Fleischhacker et al. | 5,882,302 A | 3/1999 | Driscoll, Jr. et al. ......... 600/371 |
| 5,676,692 A | 10/1997 | Sanghvi et al. ................ 607/97 | 5,882,346 A | 3/1999 | Pomeranz et al. |
| 5,676,693 A | 10/1997 | Lafontaine | 5,885,278 A | 3/1999 | Fleischman |
| 5,678,550 A | 10/1997 | Bassen et al. | 5,893,848 A | 4/1999 | Negus et al. |
| 5,680,860 A | 10/1997 | Imran | 5,895,356 A | 4/1999 | Andrus et al. ................ 600/439 |
| 5,681,278 A | 10/1997 | Igo et al. | 5,895,417 A | 4/1999 | Pomeranz et al. |
| 5,681,308 A | 10/1997 | Edwards et al. | 5,897,553 A | 4/1999 | Mulier |
| 5,687,723 A | 11/1997 | Avitall | 5,897,554 A | 4/1999 | Chia et al. |
| 5,687,737 A | 11/1997 | Branham et al. | 5,899,898 A | 5/1999 | Arless et al. |
| 5,688,267 A | 11/1997 | Panescu et al. | 5,899,899 A | 5/1999 | Arless et al. |
| 5,690,611 A | 11/1997 | Swartz et al. | 5,902,289 A | 5/1999 | Swartz et al. |
| 5,697,536 A | 12/1997 | Eggers et al. | 5,904,711 A | 5/1999 | Flom et al. |
| 5,697,882 A | 12/1997 | Eggers et al. | 5,906,580 A | 5/1999 | Kline-Schoder et al. |
| 5,697,925 A | 12/1997 | Taylor | 5,906,587 A | 5/1999 | Zimmon |
| 5,697,927 A | 12/1997 | Imran et al. | 5,906,606 A | 5/1999 | Chee et al. |
| 5,697,928 A | 12/1997 | Walcott et al. | 5,908,029 A | 6/1999 | Knudson et al. |
| 5,707,349 A | 1/1998 | Edwards ........................ 604/22 | 5,916,213 A | 6/1999 | Haissaguerre et al. |
| 5,713,942 A | 2/1998 | Stern | 5,916,214 A | 6/1999 | Cosio et al. |
| 5,716,389 A | 2/1998 | Walinsky et al. | 5,921,924 A | 7/1999 | Avitall |
| 5,718,241 A | 2/1998 | Ben-Haim et al. | 5,921,982 A | 7/1999 | Lesh et al. |
| 5,718,701 A | 2/1998 | Shai et al. | 5,927,284 A | 7/1999 | Borst et al. |
| 5,718,702 A | 2/1998 | Edwards ........................ 606/41 | 5,928,169 A | 7/1999 | Schätzle et al. ................. 601/2 |
| 5,720,719 A | 2/1998 | Edwards et al. ................ 604/22 | 5,928,191 A | 7/1999 | Houser et al. |
| 5,720,775 A | 2/1998 | Lanard | 5,931,810 A | 8/1999 | Grabek |
| 5,722,402 A | 3/1998 | Swanson et al. | 5,931,848 A | 8/1999 | Saadat |
| 5,728,094 A | 3/1998 | Edwards ........................ 606/41 | 5,938,608 A | 8/1999 | Bieger et al. ................. 600/439 |
| 5,730,074 A | 3/1998 | Peter | 5,954,661 A | 9/1999 | Greenspon et al. |
| 5,730,127 A | 3/1998 | Avitall | 5,971,980 A | 10/1999 | Sherman |
| 5,730,704 A | 3/1998 | Avitall | 5,971,983 A | 10/1999 | Lesh |
| 5,730,719 A | 3/1998 | Edwards ........................ 604/22 | 5,984,881 A | 11/1999 | Ishibashi et al. ................. 601/2 |
| 5,733,280 A | 3/1998 | Avitall | 5,984,882 A | 11/1999 | Rosenschein et al. .......... 601/2 |
| 5,733,315 A | 3/1998 | Burdette et al. ................ 607/97 | 5,993,447 A | 11/1999 | Blewett et al. |
| 5,735,280 A | 4/1998 | Sherman et al. ......... 128/600.03 | 6,004,269 A | 12/1999 | Crowley et al. .............. 600/439 |
| 5,735,290 A | 4/1998 | Nelson et al. | 6,006,134 A | 12/1999 | Hill et al. |

| | | | |
|---|---|---|---|
| 6,007,499 A | 12/1999 | Martin et al. ............... 601/3 |
| 6,012,457 A | 1/2000 | Lesh ........................ 128/898 |
| 6,016,811 A | 1/2000 | Knopp et al. |
| 6,024,740 A | 2/2000 | Lesh et al. ............... 606/34 |
| 6,026,816 A | 2/2000 | McMillan et al. ......... 128/898 |
| 6,039,694 A | 3/2000 | Larson et al. ............ 600/459 |
| 6,042,556 A | 3/2000 | Beach et al. |
| 6,056,745 A | 5/2000 | Panescu et al. |
| 6,063,081 A | 5/2000 | Mulier |
| 6,071,279 A | 6/2000 | Whayne et al. |
| 6,088,894 A | 7/2000 | Oakley |
| 6,096,033 A | 8/2000 | Tu et al. ................... 606/31 |
| 6,096,037 A | 8/2000 | Mulier |
| 6,113,559 A * | 9/2000 | Klopotek ................. 601/3 |
| 6,113,592 A | 9/2000 | Taylor |
| 6,117,101 A | 9/2000 | Diederich et al. |
| 6,120,496 A | 9/2000 | Whayne et al. |
| 6,126,619 A | 10/2000 | Peterson et al. ............ 601/2 |
| 6,126,657 A | 10/2000 | Edwards et al. ............ 606/45 |
| 6,135,971 A | 10/2000 | Hutchinson et al. .......... 601/3 |
| 6,142,993 A | 11/2000 | Whayne et al. |
| 6,142,994 A | 11/2000 | Swanson et al. |
| 6,146,379 A | 11/2000 | Fleischman |
| 6,152,920 A | 11/2000 | Thompson et al. |
| 6,161,543 A | 12/2000 | Cox et al. ................. 128/898 |
| 6,165,174 A | 12/2000 | Jacobs et al. |
| 6,174,280 B1 | 1/2001 | Oneda et al. ............... 600/121 |
| 6,190,381 B1 | 2/2001 | Olsen et al. ............... 606/32 |
| 6,206,831 B1 | 3/2001 | Suorsa et al. .............. 600/439 |
| 6,210,355 B1 | 4/2001 | Edwards et al. ............ 604/22 |
| 6,217,528 B1 | 4/2001 | Koblish et al. |
| 6,217,530 B1 | 4/2001 | Martin et al. .............. 601/2 |
| 6,217,576 B1 | 4/2001 | Tu et al. |
| 6,224,592 B1 | 5/2001 | Eggers et al. |
| 6,231,518 B1 | 5/2001 | Grabek et al. |
| 6,235,024 B1 | 5/2001 | Tu ............................. 606/41 |
| 6,237,605 B1 | 5/2001 | Vaska et al. .............. 128/898 |
| 6,238,347 B1 | 5/2001 | Nix et al. |
| 6,238,393 B1 | 5/2001 | Mulier |
| 6,241,753 B1 | 6/2001 | Knowlton ................. 607/99 |
| 6,245,061 B1 | 6/2001 | Panescu et al. |
| 6,245,064 B1 | 6/2001 | Lesh et al. ............... 606/34 |
| 6,245,065 B1 | 6/2001 | Panescu et al. |
| 6,251,092 B1 | 6/2001 | Qin et al. |
| 6,251,128 B1 | 6/2001 | Knopp et al. |
| 6,254,599 B1 | 7/2001 | Lesh et al. ............... 606/41 |
| 6,266,564 B1 | 7/2001 | Hill et al. |
| 6,270,471 B1 | 8/2001 | Hechel et al. |
| 6,293,943 B1 | 9/2001 | Panescu et al. |
| 6,296,619 B1 | 10/2001 | Brisken et al. |
| 6,302,880 B1 | 10/2001 | Schaer |
| 6,305,378 B1 | 10/2001 | Lesh ........................ 128/898 |
| 6,309,355 B1 | 10/2001 | Cain et al. ................ 600/439 |
| 6,311,692 B1 | 11/2001 | Vaska et al. .............. 128/898 |
| 6,312,383 B1 | 11/2001 | Lizzi et al. |
| 6,314,962 B1 | 11/2001 | Vaska et al. .............. 128/898 |
| 6,314,963 B1 | 11/2001 | Vaska et al. .............. 128/898 |
| 6,315,732 B1 | 11/2001 | Suorsa et al. |
| 6,315,741 B1 | 11/2001 | Martin et al. ............. 601/3 |
| 6,325,769 B1 | 12/2001 | Klopotek ................. 601/2 |
| 6,325,797 B1 | 12/2001 | Stewart et al. |
| 6,328,736 B1 | 12/2001 | Mulier |
| 6,332,881 B1 | 12/2001 | Carner et al. |
| 6,358,248 B1 | 3/2002 | Mulier |
| 6,361,531 B1 * | 3/2002 | Hissong ................... 606/27 |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,374,132 B1 | 4/2002 | Acker et al. ............. 600/411 |
| 6,383,151 B1 | 5/2002 | Diederich et al. |
| 6,385,472 B1 | 5/2002 | Hall et al. |
| 6,398,792 B1 | 6/2002 | O'Connor |
| 6,409,720 B1 * | 6/2002 | Hissong et al. ............ 606/27 |
| 6,409,722 B1 | 6/2002 | Hoey |
| 6,413,254 B1 * | 7/2002 | Hissong et al. ............ 606/27 |
| 6,419,648 B1 | 7/2002 | Vitek et al. |
| 6,425,867 B1 | 7/2002 | Vaezy et al. |
| 6,430,426 B2 | 8/2002 | Avitall |
| 6,432,067 B1 | 8/2002 | Martin et al. .............. 601/2 |
| 6,440,127 B2 | 8/2002 | McGovern et al. |
| 6,440,130 B1 | 8/2002 | Mulier |
| 6,443,952 B1 | 9/2002 | Mulier |
| 6,447,443 B1 | 9/2002 | Keogh et al. |
| 6,447,507 B1 | 9/2002 | Bednarek et al. |
| 6,451,013 B1 * | 9/2002 | Bays et al. ................. 606/27 |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. .............. 128/898 |
| 6,475,216 B2 | 11/2002 | Mulier |
| 6,477,396 B1 | 11/2002 | Mest et al. |
| 6,484,727 B1 | 11/2002 | Vaska et al. .............. 128/898 |
| 6,488,680 B1 | 12/2002 | Francischelli |
| 6,500,133 B2 | 12/2002 | Martin et al. .............. 601/3 |
| 6,500,174 B1 | 12/2002 | Maguire et al. ............ 606/41 |
| 6,502,575 B1 | 1/2003 | Jacobs et al. |
| 6,502,576 B1 | 1/2003 | Lesh ........................ 128/898 |
| 6,508,765 B2 | 1/2003 | Suorsa et al. .............. 600/439 |
| 6,508,774 B1 * | 1/2003 | Acker et al. ............... 601/2 |
| 6,514,249 B1 | 2/2003 | Maguire et al. ............ 606/41 |
| 6,514,250 B1 | 2/2003 | Jahns |
| 6,527,767 B2 | 3/2003 | Wang et al. |
| 6,537,248 B2 | 3/2003 | Mulier |
| 6,537,272 B2 | 3/2003 | Hoey |
| 6,547,788 B1 | 4/2003 | Maguire et al. ............ 606/41 |
| 6,558,382 B2 | 5/2003 | Jahns |
| 5,697,536 C1 | 6/2003 | Eggers et al. |
| 6,575,956 B1 * | 6/2003 | Brisken et al. ............ 604/500 |
| 6,584,360 B2 | 6/2003 | Francischelli |
| 6,585,732 B2 | 7/2003 | Mulier |
| 6,595,934 B1 * | 7/2003 | Hissong et al. ............. 601/3 |
| 6,610,054 B1 | 8/2003 | Edwards et al. |
| 6,610,055 B1 | 8/2003 | Swanson et al. |
| 6,610,060 B2 | 8/2003 | Mulier |
| 6,613,048 B2 | 9/2003 | Mulier |
| 6,626,855 B1 * | 9/2003 | Weng et al. ................ 601/3 |
| 6,641,579 B1 | 11/2003 | Bernardi et al. ............ 607/27 |
| 6,645,199 B1 | 11/2003 | Jenkins et al. |
| 6,645,202 B1 | 11/2003 | Vaska et al. ............... 606/41 |
| 6,648,883 B2 | 11/2003 | Francischelli |
| 6,652,515 B1 | 11/2003 | Maguire et al. ............ 606/41 |
| 6,656,175 B2 | 12/2003 | Francischelli |
| 6,663,627 B2 | 12/2003 | Francischelli |
| 6,689,128 B2 | 2/2004 | Sliwa et al. ............... 606/41 |
| 6,692,450 B1 | 2/2004 | Coleman |
| 6,699,240 B2 | 3/2004 | Francischelli |
| 6,701,391 B1 | 3/2004 | Ayat et al. ................. 710/34 |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,719,694 B2 * | 4/2004 | Weng et al. ............... 600/439 |
| 6,719,755 B2 | 4/2004 | Sliwa et al. ............... 606/41 |
| 6,736,810 B2 | 5/2004 | Hoey |
| 6,755,827 B2 | 6/2004 | Mulier |
| 6,758,847 B2 | 7/2004 | Maguire ................... 606/41 |
| 6,764,487 B2 | 7/2004 | Mulier |
| 6,773,433 B2 | 8/2004 | Stewart et al. |
| 6,776,780 B2 | 8/2004 | Mulier |
| 6,778,854 B2 | 8/2004 | Puskas |
| 6,805,128 B1 | 10/2004 | Pless et al. ............... 128/898 |
| 6,805,129 B1 | 10/2004 | Pless et al. ............... 128/898 |
| 6,807,968 B2 | 10/2004 | Francischelli |
| RE38,654 E | 11/2004 | Hill et al. |
| 6,827,715 B2 | 12/2004 | Francischelli |

| | | | |
|---|---|---|---|
| 6,840,936 B2 | 1/2005 | Sliwa et al. | 606/41 |
| RE38,705 E | 2/2005 | Hill et al. | |
| 6,849,073 B2 | 2/2005 | Hoey | |
| 6,858,026 B2 | 2/2005 | Sliwa et al. | 606/28 |
| 6,858,028 B2 | 2/2005 | Mulier | |
| 6,887,238 B2 | 5/2005 | Jahns | |
| 6,899,711 B2 | 5/2005 | Stewart et al. | |
| 6,911,019 B2 | 6/2005 | Mulier | |
| 6,912,419 B2 | 6/2005 | Hill et al. | |
| 6,916,318 B2 | 7/2005 | Francischelli | |
| 6,936,046 B2 * | 8/2005 | Hissong et al. | 606/27 |
| 6,949,097 B2 | 9/2005 | Stewart et al. | |
| 6,949,098 B2 | 9/2005 | Mulier | |
| 6,960,205 B2 | 11/2005 | Jahns | |
| 6,962,589 B2 | 11/2005 | Mulier | |
| 7,184,828 B2 | 2/2007 | Hill et al. | |
| 7,338,434 B1 | 3/2008 | Haarstad et al. | |
| 2002/0138109 A1 | 9/2002 | Keogh et al. | |
| 2003/0045872 A1 | 3/2003 | Jacobs | |
| 2003/0144656 A1 | 7/2003 | Ocel | |
| 2003/0191462 A1 | 10/2003 | Jacobs | |
| 2003/0216724 A1 | 11/2003 | Jahns | |
| 2004/0015106 A1 | 1/2004 | Coleman | |
| 2004/0015219 A1 | 1/2004 | Francischelli | |
| 2004/0044340 A1 | 3/2004 | Francischelli | |
| 2004/0049179 A1 | 3/2004 | Francischelli | |
| 2004/0078069 A1 | 4/2004 | Francischelli | |
| 2004/0082948 A1 | 4/2004 | Stewart et al. | |
| 2004/0087940 A1 | 5/2004 | Jahns | |
| 2004/0092926 A1 | 5/2004 | Hoey | |
| 2004/0138621 A1 | 7/2004 | Jahns | |
| 2004/0138656 A1 | 7/2004 | Francischelli | |
| 2004/0143260 A1 | 7/2004 | Francischelli | |
| 2004/0186465 A1 | 9/2004 | Francischelli | |
| 2004/0215183 A1 | 10/2004 | Hoey | |
| 2004/0220560 A1 | 11/2004 | Briscoe | |
| 2004/0236322 A1 | 11/2004 | Mulier | |
| 2004/0267326 A1 | 12/2004 | Ocel | |
| 2005/0010095 A1 | 1/2005 | Stewart et al. | |
| 2005/0033280 A1 | 2/2005 | Francischelli | |
| 2005/0090815 A1 | 4/2005 | Francischelli | |
| 2005/0143729 A1 | 6/2005 | Francischelli | |
| 2005/0165392 A1 | 7/2005 | Francischelli | |
| 2005/0209564 A1 | 9/2005 | Bonner | |
| 2005/0267454 A1 | 12/2005 | Hissong | |
| 2006/0009756 A1 | 1/2006 | Francischelli | |
| 2006/0009759 A1 | 1/2006 | Chrisitian | |
| 2006/0229594 A1 | 10/2006 | Francischelli | |
| 2008/0039746 A1 | 2/2008 | Hissong | |

FOREIGN PATENT DOCUMENTS

| | | |
|---|---|---|
| EP | 1 750 804 | 7/2008 |
| WO | 01-80755 | 11/2001 |
| WO | 2005-113068 | 12/2005 |
| WO | 2007-067945 | 6/2007 |
| WO | 2007-140331 | 12/2007 |

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Techique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:406-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594.

Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," J of Thorac Cardiovasc Surg, 1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:450,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94:I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8½ Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

U.S. Appl. No. 60/123,505, filed Mar. 9, 1999.

* cited by examiner

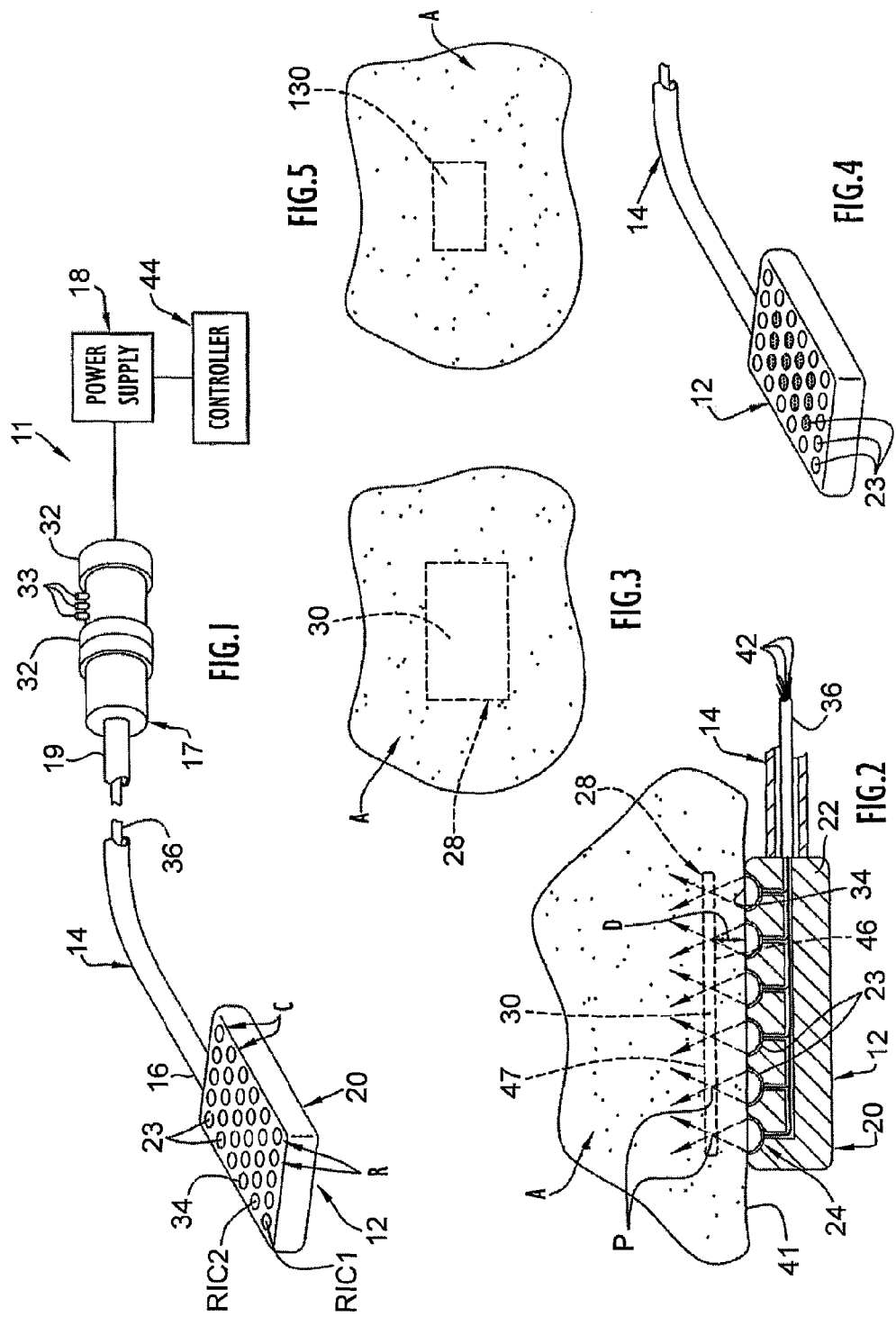

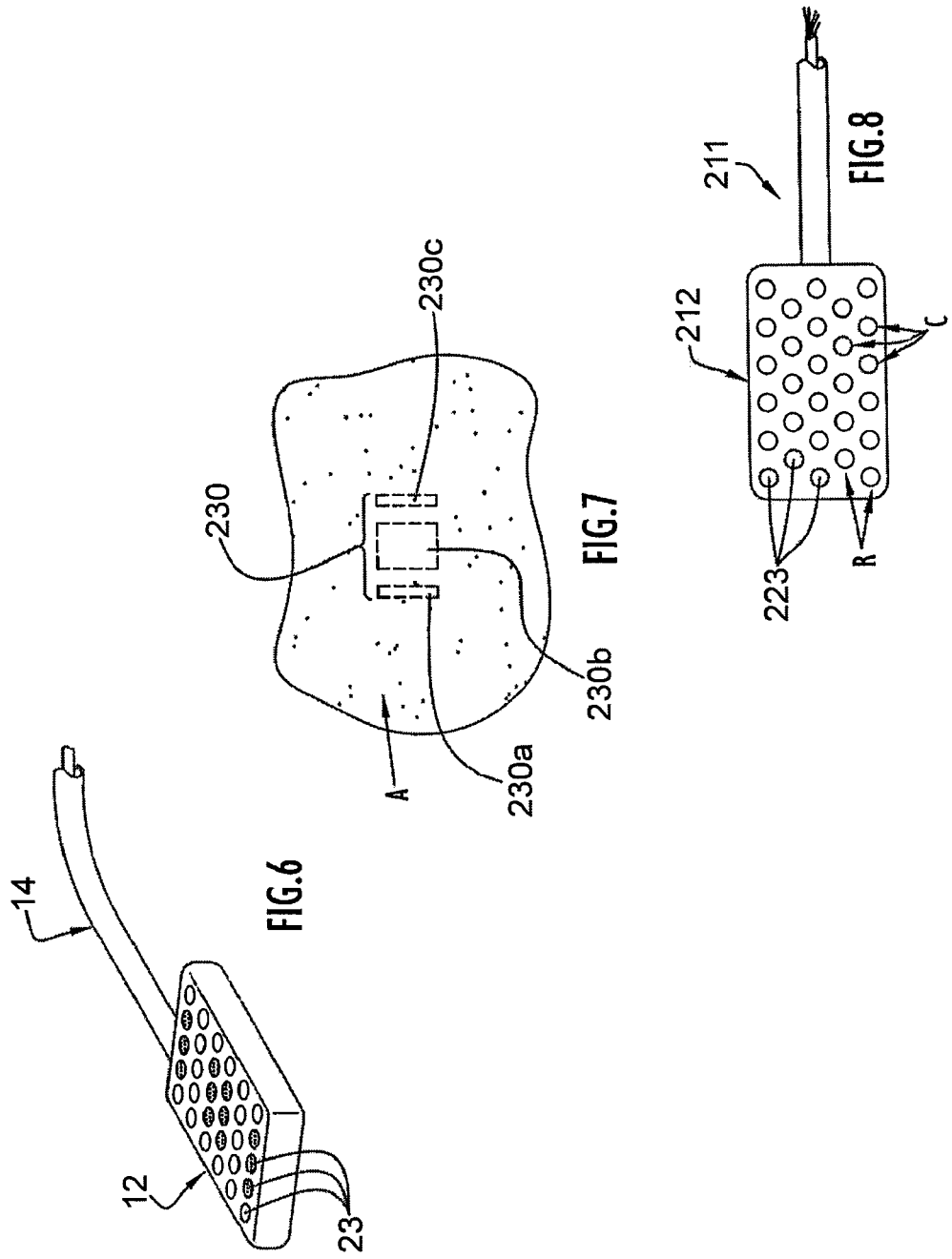

FOCUSED ULTRASOUND ABLATION DEVICES HAVING SELECTIVELY ACTUATABLE EMITTING ELEMENTS AND METHODS OF USING THE SAME

CROSS-REFERENCE TO RELATED PATENT APPLICATIONS

This application is a continuation of U.S. patent application Ser. No. 09/487,710 filed Jan. 19, 2000 now U.S. Pat. No. 6,692,450, the disclosure of which is incorporated herein by reference.

This application is related to U.S. patent applications Ser. No. 09/487,708 filed Jan. 19, 2000, now abandoned and entitled Methods of Soft Palate Reduction By Thermal Ablation Using High Intensity Focused Ultrasound, Ser. No. 09/487,707 filed Jan. 19, 2000, now U.S. Pat. No. 6,413,254 and entitled Methods of Tongue Base Reduction By Thermal Ablation Using High Intensity Focused Ultrasound, Ser. No. 09/487,709 filed Jan. 19, 2000, now abandoned and entitled Methods of Tonsil Reduction By Thermal Ablation Using High Intensity Focused Ultrasound, Ser. No. 09/487,706 filed Jan. 19, 2000, now abandoned and entitled Methods of Turbinate Or Other Soft Tissue Reduction By Thermal Ablation Using High Intensity Focused Ultrasound, Ser. No. 09/487,705 filed Jan. 19, 2000, now abandoned and entitled Methods of Skin Rejuvenation Using High Intensity Focused Ultrasound To Form An Ablated Tissue Area Containing A Plurality Of Lesions, and Ser. No. 09/488,844 filed Jan. 21, 2000, now U.S. Pat. No. 6,361,531 and entitled Focused Ultrasound Ablation Devices Having Malleable Handle Shafts and Methods of Using the Same, the disclosures of which are incorporated herein by reference.

BACKGROUND OF THE INVENTION

1. Field of the Invention

The present invention relates generally to the treatment of anatomical tissue with high intensity focused ultrasound energy and, more particularly, to focused ultrasound ablation devices having a plurality of selectively actuatable ultrasound emitting elements by which lesions of selected sizes and/or patterns are formed in anatomical tissue and to methods of thermal ablation using the same.

2. Brief Description of the Related Art

When high intensity ultrasound energy is applied to anatomical tissue, significant physiological effects may be produced in the anatomical tissue resulting from thermal and/or mechanical changes or effects in the tissue. Thermal effects include heating of the anatomical tissue; and, when the tissue is heated to a sufficiently high temperature, tissue damage such as coagulative necrosis is produced. Mechanical effects include liquefaction, cavitation and/or fragmentation of the anatomical tissue. In order to produce thermal effects in anatomical tissue, ultrasound treatment devices or applicators having ultrasound emitting members such as transducers have been used to emit ultrasound energy which is applied to anatomical tissue by positioning the ultrasound emitting members adjacent or in contact with the tissue or by coupling the ultrasound emitting members to the tissue via an acoustic coupling medium. By focusing the ultrasound energy at a specific target location, region, volume or area within the tissue, thermal effects can be confined to the specific location, region, volume or area, and such location, region, volume or area can be remote from the ultrasound emitting member.

With the use of high intensity focused ultrasound (HIFU), a discrete or defined target location, region, volume or area within a larger mass, body or area of anatomical tissue can be subjected to high intensity ultrasonic energy while surrounding non-target anatomical tissue is subjected to much lower intensity ultrasonic energy. In this manner, tissue at the target location, volume, region or area can be heated to a sufficiently high temperature so as to cause a desired thermal effect such as tissue damage, ablation, coagulation, denaturation, destruction or necrosis while tissue surrounding the target location, volume, region or area is not heated to damaging temperatures and, therefore, is preserved. Heating of the target location, volume, region or area, with the high intensity focused ultrasound, to an ablative temperature creates an ablative lesion in the tissue at the target location, volume, region or area that is subsequently naturally degraded and absorbed by the patient's body and is thusly eliminated such that the remaining body, mass or area of tissue is of smaller volume or size due to the absence of the ablated tissue.

The use of high intensity focused ultrasound to eliminate a target location, volume, region or area of tissue within a larger mass, body or area of anatomical tissue presents many advantages including minimization of trauma and pain for the patient, elimination of the need for a surgical incision, stitches and exposure of internal tissue, avoidance of damage to tissue other than that which is to be treated or removed, lack of a harmful cumulative effect from the ultrasound energy on the surrounding non-target tissue, reduction in treatment costs, elimination of the need in many cases for general anesthesia, reduction of the risk of infection and other complications, avoidance of blood loss, and the ability for high intensity focused ultrasound procedures to be performed in non-hospital sites and/or on an out-patient basis.

Various ultrasound treatment devices and/or methods for treating anatomical tissue with ultrasound have been proposed as represented by U.S. Pat. No. Re. 33,590 to Dory, No. 3,990,452 to Murry et al, No. 4,658,828 to Dory, No. 4,807, 633 to Fry, No. 4,858,613 to Fry et al, No. 4,951,653 to Fry et al, No. 4,955,365 to Fry et al, No. 5,033,456 to Pell et al, No. 5,036,855 to Fry et al, No. 5,054,470 to Fry et al, No. 5,065, 761 to Pell, No. 5,080,101 to Dory, No. 5,080,102 to Dory, No. 5,117,832 to Sanghvi et al, No. 5,134,988 to Pell et al, No. 5,143,074 to Dory, No. 5,150,711 to Dory, No. 5,150,712 to Dory, No. 5,158,070 to Dory, No. 5,222,501 to Ideker et al, No. 5,267,954 to Nita, 5,269,291 to Carter, 5,269,297 to Weng et al, 5,295,484 to Marcus et al, No. 5,304,115 to Pflueger et al, No. 5,312,328 to Nita et al, No. 5,318,014 to Carter, No. 5,342,292 to Nita et al, No. 5,354,258 to Dory, No. 5,380,274 to Nita, No. 5,391,197 to Burdette et al, No. 5,397, 301 to Pflueger et al, No. 5,409,002 to Pell, No. 5,417,672 to Nita et al, No. 5,431,621 to Dory, No. 5,431,663 to Carter, No. 5,447,509 to Mills et al, No. 5,474,530 to Passafaro et al, No. 5,492,126 to Hennige et al, No. 5,501,655 to Rolt et al, No. 5,520,188 to Hennige et al, No. 5,542,917 to Nita et al, No. 5,620,479 to Diederich, No. 5,676,692 to Sanghvi et al, No. 5,728,094 to Edwards, No. 5,730,719 to Edwards, No. 5,733, 315 to Burdette et al, No. 5,735,280 to Sherman et al, No. 5,738,114 to Edwards, No. 5,746,224 to Edwards, No. 5,762, 066 to Law et al, No. 5,800,379 to Edwards, No. 5,800,429 to Edwards, No. 5,800,482 to Pomeranz et al, No. 5,807,308 to Edwards, No. 5,817,049 to Edwards, No. 5,823,197 to Edwards, No. 5,827,277 to Edwards, No. 5,843,077 to Edwards, No. 5,871,524 to Knowlton, No. 5,873,845 to Cline et al, No. 5,873,902 to Sanghvi et al, No. 5,879,349 to Edwards, No. 5,882,302 to Driscoll, Jr. et al, No. 5,895,356 to Andrus et al and No. 5,938,608 to Bieger et al.

In particular, focused ultrasound ablation devices used to thermally damage, ablate, coagulate, denature, cauterize, necrotize or destroy a target volume of tissue are exemplified by U.S. Pat. No. Re. 33,590 to Dory, No. 4,658,828 to Dory, No. 4,807,633 to Fry, No. 4,858,613 to Fry et al, No. 4,951, 653 to Fry et al, No. 4,955,365 to Fry et al, No. 5,036,855 to Fry et al, No. 5,054,470 to Fry et al, No. 5,080,101 to Dory, No. 5,080,102 to Dory, No. 5,117,832 to Sanghvi et al, No. 5,143,074 to Dory, No. 5,150,711 to Dory, No. 5,150,712 to Dory, No. 5,295,484 to Marcus et al, No. 5,354,258 to Dory, No. 5,391,197 to Burdette et al, No. 5,431,621 to Dory, No. 5,492,126 to Hennige et al, No. 5,501,655 to Rolt et al, No. 5,520,188 to Hennige et al, No. 5,676,692 to Sanghvi et al, No. 5,733,315 to Burdette et al, No. 5,762,066 to Law et al, No. 5,871,524 to Knowlton, No. 5,873,845 to Cline et al, No. 5,873,902 to Sanghvi et al, No. 5,882,302 to Driscoll, Jr. et al, No. 5,895,356 to Andrus et al and No. 5,938,608 to Bieger et al. The focused ultrasound ablation devices are used to ablate various target areas in or on the bodies of patients including the brain, prostate, heart, urethra, blood vessels, deep seated tissue and tumors, liver, kidney, skin, breast, stomach and pancreas.

Ablation of anatomical tissue of the head and/or neck in order to reduce or eliminate such tissue in the treatment of various airway related disorders has also been proposed as illustrated by U.S. Pat. No. 5,423,812 to Ellman et al, Nos. 5,456,662, 5,514,131, 5,624,439, 5,674,191, 5,707,349, 5,718,702, 5,728,094, 5,730,719, 5,738,114, 5,743,870, 5,743,904, 5,746,224, 5,800,379, 5,800,429, 5,807,308, 5,817,049, 5,823,197, 5,827,277, 5,843,077 and 5,879,349 to Edwards and WO 97/43970. The areas ablated include the soft palate, uvula, tongue, tonsils, adenoids and turbinates. U.S. Pat. No. 5,423,812 relates to electrosurgical stripping of tissue. U.S. Pat. No. 5,456,662, No. 5,514,131, No. 5,624, 439, No. 5,674,191, No. 5,707,349, No. 5,718,702, No. 5,728,094, No. 5,730,719, No. 5,738,114, No. 5,743,870, No. 5,743,904, No. 5,746,224, No. 5,800,379, No. 5,800,429, No. 5,807,308, No. 5,817,049, No. 5,823,197, No. 5,827,277, No. 5,843,077, No. 5,879,349 and WO97/43970 disclose RF ablation using tissue penetrating electrodes. U.S. Pat. No. 5,707,349, No. 5,728,094, No. 5,730,719, No. 5,738,114, No. 5,746,224, No. 5,800,379, No. 5,800,429, No. 5,807,308, No. 5,817,049, No. 5,823,197, No. 5,827,277, No. 5,843,077 and No. 5,879,349 refer to ultrasound as a possible source of ablative energy.

Prior focused ultrasound ablation devices typically have ultrasound emitting members, commonly including transducers, for emitting ultrasound energy and focusing the ultrasound energy at target areas in anatomical tissue in order to effect thermal ablation at the target areas. Exemplary focused ultrasound ablation devices employing transducers as the ultrasound emitting members thereof are disclosed in U.S. Pat. Nos. 4,658,828 to Dory, 4,858,613, 4,951,653, 4,955, 365, 5,036,855 and 5,054,470 to Fry et al, 5,080,101 and 5,080,102 to Dory, 5,117,832 to Sanghvi et al, 5,143,074, 5,150,711 and 5,150,712 to Dory, 5,295,484 to Marcus et al, 5,354,258 to Dory, 5,391,197 to Burdette et al, 5,431,621 to Dory, 5,492,126 to Hennige et al, 5,501,655 to Rolt et al, 5,520,188 to Hennige et al, 5,676,692 to Sanghvi et al, 5,762, 066 to Law et al, 5,873,845 to Cline et al, 5,873,902 to Sanghvi et al, 5,882,302 to Driscoll, Jr. et al, 5,895,356 to Andrus et al, 5,928,169 to Schätzle et al, 5,938,608 to Bieger et al and Re. 33,590 to Dory.

Some prior focused ultrasound ablation devices employ arrays or pluralities of transducer elements as the ultrasound emitting members, respectively, as represented by U.S. Pat. Nos. 4,658,828, 5,080,101, 5,080,102, 5,143,074, 5,150,712 and Re. 33,590 to Dory, 5,391,197 to Burdette et al, 5,501,655 to Rolt et al, 5,520,188 to Hennige et al, 5,928,169 to Schätzle et al and 5,938,608 to Bieger et al. U.S. Pat. Nos. 4,658,828, 5,080,101, 5,080,102, 5,150,712, 5,501,655, 5,520,188, 5,928,169, 5,938,608 and Re. 33,590 disclose the transducer elements as being actuated or driven in phase-offset relation to one another in order to change the location at which the ultrasound energy is focused in anatomical tissue. U.S. Pat. Nos. 5,746,224 and 5,800,429 to Edwards disclose an energy delivery device comprising one or more ring electrodes to which RF energy may be independently delivered to effect thermal ablation of tissue. Ultrasound is merely referred to as a possible source of ablative energy.

In order to enhance the efficacy of focused ultrasound ablation procedures, it would be desirable to customize or tailor lesions to be formed in particular patients. For example, it would be desirable for a single focused ultrasound ablation device to be capable of forming lesions of various sizes and/or configurations or patterns in anatomical tissue including lesions of various irregular or discontinuous patterns. Also, it would be desirable for a focused ultrasound ablation device to be capable of forming a lesion comprising disconnected lesion segments. By providing a focused ultrasound ablation device having the foregoing attributes, optimum lesion characteristics can be selected for particular patients based on assessments made by surgeons or other medical personnel at the time of surgery. However, prior focused ultrasound ablation devices, as exemplified by the above-mentioned patents, do not provide focused ultrasound emitting members having the foregoing attributes.

SUMMARY OF THE INVENTION

Accordingly, it is a primary object of the present invention to overcome the various disadvantages of prior focused ultrasound ablation devices.

It is also an object of the present invention to provide a focused ultrasound ablation device having an ultrasound emitting member capable of forming lesions of various preselected configurations in anatomical tissue.

Another object of the present invention is to provide a focused ultrasound ablation device having an ultrasound emitting member capable of forming a lesion comprising a plurality of disconnected lesion segments in anatomical tissue.

A further object of the present invention is to selectively actuate less than all of a plurality of ultrasound emitting elements of a focused ultrasound emitting member in order to form a lesion of selected size and/or configuration in anatomical tissue.

An additional object of the present invention is to increase the diversity of sizes and/or configurations of lesions capable of being formed in anatomical tissue.

It is also an object of the present invention to electronically control the actuation of selected ones of a plurality of ultrasound emitting elements of a focused ultrasound emitting member to form a lesion of optimal size and/or configuration in anatomical tissue of a patient.

The present invention also has as an object to provide a multi-array transducer including a plurality of transducer elements that are selectively actuatable to form lesions of various preselected sizes and/or configurations in patients.

Some of the advantages of the present invention are that the outcome of ultrasound ablation procedures in various areas of the body is greatly enhanced, a single focused ultrasound ablation device can optimally be used in various ablation procedures in various areas of the body, anatomical tissue around, between or surrounding the lesion segments can be left lesion free, a focused ultrasound emitting member having a particular array of transducer elements can be used to form lesions corresponding in size and/or configuration to the size and/or configuration of the array as well as lesions having sizes and/or configurations different from the size and/or configuration of the array, the focused ultrasound emitting member can be coupled with a handle for hand-held use and operation thereof, the focused ultrasound ablation device does not have to be customized for use in a specific area of the body, and the focused ultrasound emitting member can be provided in a focused ultrasound ablation device provided as a standardized instrument capable of being used in or on a wide variety of areas of patients' bodies.

These and other objects, advantages and benefits are realized with the present invention as generally characterized in a focused ultrasound ablation device including an ultrasound emitting member having a plurality of individual ultrasound emitting elements arranged thereon in an array. The ultrasound emitting elements are actuatable to emit ultrasound energy and focus the emitted ultrasound energy a predetermined distance from the ultrasound emitting member such that the ultrasound energy is focused within anatomical tissue adjacent which the ultrasound emitting member is placed. The ultrasound energy is of relatively higher intensity where focused within the anatomical tissue, causing the anatomical tissue to be heated to an ablative temperature to form an internal lesion within the tissue. The ultrasound emitting elements are selectively, independently actuatable, allowing selected ones of the ultrasound emitting elements to be actuated to emit ultrasound energy to obtain a lesion of desired or selective size and/or surface configuration in the tissue of a particular patient. The lesion size and/or surface configuration corresponds to the locations and/or pattern of the ultrasound emitting elements selected for actuation. In this manner, lesion characteristics can be optimally selected for particular patients and particular ablation procedures to be performed. In a preferred embodiment, the ultrasound emitting elements are transducer elements including piezoelectric elements that emit ultrasound energy in response to an electric signal supplied thereto, and selected ones of the transducer elements are selected for actuation by selectively coupling the selected elements to an electrical signal.

A method of thermal ablation of anatomical tissue according to the present invention is generally characterized by the steps of selecting selected ones of a plurality of ultrasound emitting elements, arranged in an array on an ultrasound emitting member, for actuation to emit ultrasound energy in accordance with a desired size and/or configuration of a lesion to be formed in anatomical tissue of a patient, positioning the ultrasound emitting member adjacent or in contact with the anatomical tissue at a location aligned with a desired site for the lesion in the tissue, actuating the selected ones of the ultrasound emitting elements to emit ultrasound energy, focusing the ultrasound energy with the selected ones of the ultrasound emitting elements so that the ultrasound energy is focused a predetermined depth within the tissue and heating the tissue with the focused ultrasound energy to form an internal lesion within the tissue having the desired size and/or configuration.

BRIEF DESCRIPTION OF THE DRAWINGS

FIG. 1 is a broken perspective view, partly schematic, illustrating a focused ultrasound ablation device incorporating a focused ultrasound emitting member according to the present invention.

FIG. 2 is a broken side view, partly in section, depicting actuation of all of a plurality of ultrasound emitting elements of the ultrasound emitting member to emit ultrasound energy and focus the ultrasound energy in anatomical tissue to form a lesion.

FIG. 3 is a broken top view, illustrating the surface configuration of the lesion of FIG. 2.

FIG. 4 is a broken perspective view illustrating actuation of selected ones of the plurality of ultrasound emitting elements.

FIG. 5 is a broken top view illustrating the surface configuration of a lesion formed in tissue with the focused ultrasound emitting member when actuated as shown in FIG. 4.

FIG. 6 is a broken perspective view illustrating actuation of selected alternative ones of the plurality of ultrasound emitting elements.

FIG. 7 is a broken top view illustrating the surface configuration of a lesion formed in tissue with the focused ultrasound emitting member when actuated as depicted in FIG. 6.

FIG. 8 is a perspective side view illustrating an alternative focused ultrasound ablation device incorporating a modified focused ultrasound emitting member according to the present invention.

DESCRIPTION OF THE PREFERRED EMBODIMENTS

A high intensity focused ultrasound ablation device 11 incorporating a focused ultrasound emitting member 12 according to the present invention is illustrated in FIG. 1. The focused ultrasound ablation device 11 includes ultrasound emitting member or element 12, an elongate handle shaft or handle body 14 having a distal end 16 at which the ultrasound emitting member 12 is disposed and a handle or handpiece 17 coupled to a proximal end 19 of handle shaft 14. As shown in FIG. 2, the ultrasound emitting member 12 includes a transducer 20 carried by a housing 22 and capable of generating and emitting ultrasound energy in response to being supplied with electrical power from a power supply 18. The transducer 20 includes a plurality of individual ultrasound emitting elements, transducers or transducer elements 23, each including a piezoelectric element 24 that vibrates to produce ultrasound energy when electrical current is supplied thereto. The transducer elements 23 have a focusing configuration or geometry that results in the ultrasound energy produced thereby being focused a fixed distance from the ultrasound emitting member 12. The transducer elements 23 have a partial spherical, concave configuration causing the ultrasound energy generated thereby to be focused, as shown by arrows in FIG. 2, at focusing zones P.

The transducer elements 23 are arranged in an array on or in housing 22; and, therefore, the transducer 20 may be considered a multi-array transducer. In the case of focused ultrasound emitting member 12, the transducer elements 23 are arranged in a planar array of five rows R and six columns C, although the transducer elements can be arranged in any number of rows and columns depending on the number of transducer elements provided in the ultrasound emitting member. In the case of focused ultrasound emitting member 12, each row R has an equal number of transducer elements, and each column C has an equal number of transducer elements. It should be appreciated that any number of transducer elements can be provided in each row and column and that the numbers of transducer elements provided in each row and column can be the same or different. The transducer elements 23 can be referenced by their location in the array. For example, the transducer elements in the first row, first column can be designated transducer element R1C1, the transducer elements in the first row, second column can be designated transducer element R1C2 and so on. The transducer elements of each row are disposed close to one another, and the transducer elements of each column are disposed close to one another such that there is minimal space between adjacent transducer elements 23. As explained further below, the transducer elements 23 are selectively, independently actuatable to selective emit or not emit ultrasound energy.

The transducers 23 can be designed in various ways as known in the art. In the case of transducer 20, the transducers or transducer elements 23 each comprise a layer of piezoelectric material carried by housing 22 and forming the piezoelectric elements 24. The piezoelectric elements 24 are recessed from a planar external surface 34 of housing 22. The piezoelectric elements 24 are curved in a direction inwardly of surface 34 such that ultrasound energy generated by elements 24 is emitted from focused ultrasound emitting member 12 in a direction perpendicular to surface 34 for focusing at the focusing zones P, which are spaced outwardly of surface 34. Accordingly, surface 34 is an active surface or face of the ultrasound emitting member 12 which, when positioned externally adjacent or in contact with a mass, body or area of anatomical tissue A, results in the ultrasound energy emitted by transducer 20 being focused at zones P, which will be disposed within the anatomical tissue A as shown in FIG. 2.

Each focusing zone P is in line with a central axis of the corresponding piezoelectric element 24. Each focusing zone P is disposed a fixed predetermined distance D from a plane containing the surface 34, the distance D for each focusing zone P being perpendicular to the surface 34. Therefore, the focusing zones P will also be disposed a predetermined perpendicular distance or a calculable or determinable perpendicular distance from an external tissue surface 41 of tissue A with which the surface 34 is placed in contact or adjacent thereto. Where the surface 34 is placed in contact with the external tissue surface 41, the perpendicular distance that zones P are disposed from external tissue surface 41 will be the same as the predetermined distance D as shown in FIG. 2. Where the surface 34 is not placed in contact with the external tissue surface 41 but, rather, is spaced from the external tissue surface 41 by a known amount, for example, the perpendicular distance that zones P are disposed from the external tissue surface 41 will correspond to distance D minus the distance that the surface 34 is spaced from the external tissue surface 41. Where the surface 34 is spaced from the external tissue surface 41, an acoustic coupling medium can be disposed between the external tissue surface 41 and the member 12 as disclosed in the patent applications incorporated herein by reference and entitled Methods of Soft Palate Reduction By Thermal Ablation Using High Intensity Focused Ultrasound, Methods of Tongue Base Reduction By Thermal Ablation Using High Intensity Focused Ultrasound, Methods of Tonsil Reduction By Thermal Ablation Using Soft Tissue Reduction By Thermal Ablation Using High Intensity Focused Ultrasound, Methods of Skin Rejuvenation By Thermal Stimulation Using High Intensity Focused Ultrasound and Focused Ultrasound Ablation Devices Having Malleable Handle Shafts and Methods of Using the Same.

Since the ultrasound is focused at zones P, the ultrasound is of greater or higher intensity at focusing zones P and is thusly focused or concentrated at the focusing zones P, causing tissue A at the focusing zones P to be heated to an ablative temperature. When all of the transducer elements 23 are actuated, as shown in FIG. 2, heating of tissue A will occur at a focusing zone P for each transducer element 23. since the transducer elements 23 are disposed close to one another, the areas of tissue A between the focusing zones P are also heated to an ablative temperature due to the dispersal or spread of heat from the focusing zones P. Accordingly, a discrete, definitive lesion 30 is formed in the tissue A at a lesion or target area 28 while the temperature of the tissue A surrounding the lesion or target area 28 remains below damaging levels such that the surrounding tissue is undamaged and preserved. When all of the transducer elements 23 are actuated, a target or lesion area of specific configuration and size is created within the body, mass or area of anatomical tissue A for the transducer 20 in accordance with the intensity level of the emitted ultrasound energy and the duration or time of ultrasound energy delivery to the tissue. Accordingly, a lesion 30 having a specific length, width and depth is formed at the target or lesion area 28. FIGS. 2 and 3 illustrate the lesion 30 formed in tissue A when all of the transducer elements 23 are actuated. The lesion 30 has a generally rectangular configuration with a predetermined length and width dictated by the configuration of the array and a predetermined depth dictated by the length of the zones P.

The housing 22 can have various external configurations and sizes in accordance with the size, configuration and design of transducer 20 and the array in which the transducer elements 23 are arranged. In the case of ultrasound emitting member 12, the housing 22 has a generally rectangular external configuration with rounded or blunt corners and/or edges to avoid damage to anatomical tissue. It should be appreciated that the transducer elements 23 can be disposed within the housing with the ultrasound energy generated by transducer 20 being transmitted or emitted through or from a wall of the housing, such wall being made of material through which ultrasound energy can pass and defining the active face for the ultrasound emitting member. Of course, a surface of the transducer itself can define the active face for the ultrasound emitting member. The active face 34 for ultrasound emitting member 12 is parallel to a longitudinal axis of member 12 so that the predetermined or determinable distances for zones P beyond the active face 34 and the external tissue surface 41 are perpendicular to the longitudinal axis. It should be appreciated, however, that the active face 34 can be disposed at various angles to the longitudinal axis whereby the predetermined or determinable distances for zones P beyond the active face and the external tissue surface 41 may be perpendicular to the active face but non-perpendicular to the longitudinal axis. The active face 34 may be rigid or flexible or deformable depending on procedural use. The active face and/or transducer 20 may be designed to conform to the shape of the tissue surface against which the active face is placed. Of course, where soft tissue is being ablated, the soft tissue may conform to the shape of the active face 34 and/or transducer 20 where the active face 34 and/or transducer 20 is/are more rigid than the tissue.

The handle shaft 14 comprises an elongate, hollow or tubular member of sufficient length to position the ultrasound emitting member 12 at various operative sites in or on the body of a patient while the handle 17 is maintained at a remote location, typically externally of the patient's body. Preferably, the handle shaft 14 is malleable as disclosed in the application entitled Focused Ultrasound Ablation Devices Having Malleable Handle Shafts and Methods of Using the Same, the disclosure of which is incorporated herein by reference. The distal end 16 of handle shaft 14 is coupled with the ultrasound emitting member 12 by being disposed on or within an end wall of housing 22 or by extending through the end wall of housing 22 to be disposed within the housing.

The handle 17 has a forward end coupled to the proximal end 19 of handle shaft 14 and has a rearward end. The handle 17 preferably has a configuration to facilitate grasping by a surgeon or other operator. In the case of focused ultrasound ablation device 11, the handle 17 has a cylindrical body with raised, external annular segments 32. The segments 32 are longitudinally spaced from one another, and one or more controls or switches 33, such as push button controls or switches 33, may be disposed on handle 17 between spaced segments 32. The one or more controls or switches 33, where provided, may be used to effect operation of the focused ultrasound ablation device 11. It should be appreciated that the handle 17 can be provided without controls or switches in which case operation of the focused ultrasound ablation device may be effected by one or more controls or switches located on the power supply, a controller 44 and/or a dedicated structure such as a foot pedal. Where the one or more controls or switches are provided on the handle 17, as illustrated for focused ultrasound ablation device 11, the one or more controls or switches is/are desirably placed at a location on handle 17 amenable to convenient operation thereof by the hand of the surgeon or other operator grasping the handle 17. As shown in FIG. 1, the push button controls or switches 33 are accessible and operable by a finger of the hand grasping the handle 17 for one-handed operation of ablation device 11. The proximal end 19 of handle shaft 14 is coupled with handle 17 at the forward end thereof and, in particular, at a forward wall of the handle. The proximal end 19 may be disposed on or within the forward wall or may extend through the forward wall to be disposed within the handle 17. With the proximal end 19 of the handle shaft 14 thusly coupled to the handle 17, the longitudinal axis of handle 17 is coaxially aligned with the longitudinal axis of handle shaft 14 at proximal end 19.

One or more electrical transmission wires 42 is/are connected to the transducer 20 and extend through the handle shaft 14 for connection with power supply 18 in order to transmit or supply electric current from the power supply 18 to the transducer 20. The power supply 18 may be disposed partly or entirely in the handle 17, or may be provided separately as a console or unit coupled to the handle shaft 14 or to handle 17 via one or more appropriate transmission wires, which may be the same or different from the one or more transmission wires 42. For example, an electrical cord of suitable length may be removably coupled between the handle 17 and the power supply 18. The power supply 18 can be designed in various ways as a source or supply of electricity to activate or excite transducer 20 to generate and emit ultrasound energy. For example, the power supply 18 is designed to provide high frequency alternating electrical current to the transducer 20 via the one or more transmission wires 42. The power supply 18 may include an RF generator, with or without an amplifier, providing a constant current source. Electrical current provided by the power supply 18 is selectively discharged into all or selected ones of the piezoelectric elements 24, producing vibration of all or selected ones of the element 24 and, therefore, producing acoustic or ultrasonic waves or energy. The power supply 18 may be separate from the handle 17 but may be operated via controls 33 of handle 17.

In the case of focused ultrasound ablation device 11, a transmission wire 42 is provided for each piezoelectric element 24. As shown in FIG. 2, each transmission wire 42 is connected to its corresponding piezoelectric element 24 and to the power supply 18 so that the transducer elements 23 are individually driven by or supplied with current from the power supply 18. The transmission wires 42 are disposed in respective passages within housing 22 and may be disposed within a sheath or sleeve 36 extending through shaft 14. The transmission wires 42 are connected to switches (not shown), respectively, for controlling the supply or transmission of current from the power supply 18 to the piezoelectric elements 24, respectively. The switches can be incorporated in the ultrasound emitting member 12, the power supply 18 or the controller 44.

The controller or control unit 44, shown schematically in FIG. 1, controls the supply of power from power supply 18 to transducer 20 so that the transducer 20 can be driven to deliver various intensity levels of ultrasound energy for various durations, periods or lengths of time. In particular, the controller 44 controls the supply of power from power supply 18 to the individual piezoelectric elements 24 so that the transducer elements 23 can be individually driven or actuated to emit ultrasound energy. The controller, which may be designed as part of the power supply 18, will typically include a control panel and display monitor, a switch for current control, an input mechanism such as a keyboard, and/or a microprocessor including memory, storage and data processing capabilities for performing various functions. The controller 44 is capable of selectively activating the switches to effect actuation of all or selected ones of the plurality of transducer elements 23. For example, switches on the controller 44 and/or the controller keyboard can be used to selectively couple and decouple the individual transducer elements 23 with the electrical drive signal or current from the power supply 18. Input to the controller 44 provided by the surgeon or other medical personnel determines the transducer elements 23 to be actuated. For example, data entered via the controller keyboard is used to identify the particular transducer elements 23 to be actuated, the transducer elements 23 being identified, for example, by their location or position in the array as explained above. In this manner, the switches of selected transducer elements 23 can be activated to permit transmission of electrical current from the power supply 18 to the piezoelectric elements 24 of the selected transducer elements while the switches of other selected transducer elements 23 can remain deactivated to prevent transmission of electrical current thereto when the power supply is actuated or switched to an "on" mode. It should be appreciated that various components and/or methodology can be incorporated in the device 11, including the power supply 18 and/or the controller 44, to permit selective actuation of selected ones of the transducer elements 23 and that such components and/or methodology would be within the purview of one skilled in the art.

Various transducers can be used in the focused ultrasound ablation devices of the present invention. The transducer can include an annular array, a linear array and/or a curved linear array of transducer elements. The piezoelectric elements can be made of various piezoelectric materials such as PZT crystal materials, hard lead, zirconate/lead titanium piezoelectric ceramic, or lithium-niobate piezoceramic material. The array of piezoelectric elements can be of various sizes or surface configurations to obtain lesions of various sizes with an array of larger surface area generally providing more ultrasound energy and a larger lesion size than an array of smaller surface area. The frequency ranges of the transducer and/or the individual transducer elements can vary depending on clinical needs. Preferably, the transducer frequency will allow thermal ablation of anatomical tissue to be effected at the target area in response to the application or delivery of ultrasound energy for a relatively short duration or length of time.

It should be appreciated that the high intensity focused ultrasound ablation device 11 can be provided with imaging capabilities for visualizing an operative site at which the focused ultrasound ablation device 11 is to be used, for visualizing guidance and/or positioning of the ultrasound emitting member 12 at the operative site and/or for examination and diagnosis. The focused ultrasound ablation device 11 can be designed to provide the imaging capabilities and can thusly be used for both therapy and imaging. Observation of a detected image can be obtained at a location remote from the operative site. For example, the ultrasound emitting member 12 can be provided with an ultrasound imaging transducer as described in the applications incorporated herein by reference. Conventional optical guidance mechanisms, such as fiber optic mechanisms, can be used in or with the high intensity focused ultrasound ablation device 11, such as in or on the focused ultrasound ablation device 11, to provide remote visualization, and such optical guidance mechanisms can be separate from or formed as part of the ultrasound emitting members. The high intensity focused ultrasound ablation device can be provided with a viewing device such as an eyepiece on the handle shaft or on the handle or a video monitor for viewing an image of the operative site from the remote location, typically externally of the patient's body.

The focused ultrasound ablation devices of the present invention is used to ablate a target or lesion area within a larger mass, body or area of tissue to create an internal ablative lesion that is capable of being naturally degraded and absorbed by a patient's body. As the lesion is absorbed, the tissue shrinks or decreases in size. In this manner, the size or volume of the mass, body or area of tissue can be reduced and/or the configuration of the mass, body or area of tissue can be changed for various therapeutic purposes.

In a thermal ablation procedure utilizing focused ultrasound ablation device 11, the controller 44 is instructed to effect actuation of selected transducer elements 23 in accordance with the size and/or pattern of a lesion desired to be formed in tissue of a particular patient. In the procedure illustrated in FIG. 2, all of the transducer elements 23 are to be actuated; and, accordingly, input to the controller 44 made by the surgeon or other medical personnel designates all of the transducer elements 23 to be actuated by the power supply 18 to obtain a lesion of continuous surface area. The surface or active face 34 is positioned in contact with an external tissue surface 41 of tissue A of the patient at a location or operative site on tissue A corresponding to or aligned with a desired location or site for a subsurface lesion as shown in FIG. 2. Once the surface 34 is positioned in contact with the tissue A at the desired location, the power supply 18 is activated or switched to an "on" mode, such as by depressing a pushbutton 33. Since all of the transducer elements 23 have been designated or selected for actuation, electrical energy is transmitted from the power supply 18 to each piezoelectric element 24 via the transmission wires 42. In response thereto, the piezoelectric elements 24 vibrate and produce ultrasound energy which, due to the curved configuration of the piezoelectric elements 24, is focused at focusing zones P, within the tissue A. Accordingly, anatomical tissue A at the focusing zones P is heated to an ablative temperature and spreads or disseminates throughout the lesion or target area 28 causing a bioabsorbable subsurface or internal ablative lesion 30 to be formed in the tissue A at the target area 28 while the ultrasound emitting member 12 remains external of and does not physically penetrate the tissue A. In addition, tissue surrounding the target area 28 is not heated to damaging levels and is thusly preserved. The lesion 30 has a length, width and depth of known parameters dictated by the configuration of the array, the intensity of the ultrasound energy and the duration of ultrasound energy delivery or application to the tissue. The lesion can have various continuous or discontinuous configurations, including rectangular, square and circular configurations depending on the surface configuration of the array and/or the pattern presented by the transducer elements selected for actuation. Since the transducer elements 23 are arranged in a rectangular array, the lesion 30 is continuous or solid along a rectangular surface configuration, as shown in FIG. 3, when all the transducer elements 23 are actuated.

Due to the predetermined distance D for the focusing zones and the known parameters for the lesion 30 capable of being obtained with the transducer 20, the lesion 30 begins at a beginning or starting margin 46 located a predetermined or known depth beneath or below the external tissue surface 41 and ends at an ending margin 47 located a predetermined or known depth beneath the external tissue surface 41. The distance between the beginning and ending margins corresponds to the depth of the lesion. By selecting a transducer with the appropriate focusing zone depth in the tissue, a desired preselected thickness or depth of tissue between the beginning margin 46 and the external tissue surface 41 is disposed outside the target area 28 and is therefore undamaged and preserved. Although the length and width or other external dimensions of the lesion can be determined by the configuration of the array and/or by actuation of selected transducer elements 23, it should be appreciated that the external dimensions of the lesion can alternatively be obtained by moving the member 12 from point to point on the tissue as described in the co-pending patent applications incorporated herein by reference.

The emission of ultrasound energy by ultrasound emitting member 12 is terminated by the surgeon or other operator once a desired lesion size or amount of tissue ablation has been obtained, and the member 12 is removed from the tissue A. In order to terminate the emission of ultrasound energy by ultrasound emitting member 12, the power supply 18 is deactivated or switched to an "off" mode, such as via a pushbutton 33, so that electrical current is no longer supplied to the piezoelectric elements 24. Where one or more additional lesions are to be formed in tissue A or other tissue of the patient, the member 12 is repositioned on the tissue A or is positioned on the other tissue at another selected location or operative site, and the procedure is repeated. The lesion 30 will be naturally degraded and absorbed by the patient's body in due course, and the remaining tissue A will be smaller in bulk, size or volume than it was prior to treatment.

FIG. 4 illustrates focused ultrasound emitting member 12 when the transducer elements 23 in the outermost rows and columns of the array are not activated to emit ultrasound energy, the activated transducer elements 23 being shaded in FIG. 4. In particular, the transducer elements 23 of columns one and six and rows one and five are not actuated while the remaining transducer elements 23 are actuated to emit ultrasound energy by the power supply 18 as selected and controlled via the controller 44 as described above. The activated transducer elements 23 form a rectangular pattern or sub-array forming a subsurface lesion 130 in tissue A as shown in FIG. 5. The lesion 130 is similar to the lesion 30 except that the lesion 130 is continuous or solid along a rectangular surface configuration smaller than the rectangular surface configuration for lesion 30.

FIG. 6 is illustrative of a discontinuous "firing" pattern for the array of transducer elements 23. FIG. 6 shows the focused ultrasound emitting member 12 with selected transducer elements 23 activated to emit ultrasound energy, the activated transducer elements 23 being shaded. In FIG. 6, the transducer elements 23 at locations R2C1, R3C1, R4C1, R2C3, R3C3, R4C3, R2C4, R3C4, R4C4, R2C6, R3C6 and R4C6 are actuated to emit ultrasound energy while the remaining transducer elements 23 are decoupled from the power supply 18. FIG. 7 illustrates a lesion 230 obtained with ultrasound emitting member 12 when the transducer elements 23 are "fired" in the pattern shown in FIG. 6. As shown in FIG. 7, a discontinuous lesion 230 is formed in tissue A, the lesion 230 comprising separate, disconnected lesion segments 230a, 230b and 230c. Lesion segment 230b is centrally located between lesion segments 230a and 230c and has a length and width corresponding or substantially corresponding to the length and width of a rectangular sub-array formed by the transducer elements 23 at locations R2C3, R2C4, R3C3, R3C4, R4C3 and R4C4. Accordingly, lesion segment 230b is continuous or solid along a surface area of rectangular configuration. Lesion segments 230a and 230c are similar to one another and are disposed on opposite sides of lesion segment 230b. Lesion segments 230a and 230c are spaced from lesion segment 230b, and the tissue segments between lesion segment 230b and lesion segments 230a and 230c, respectively, are undamaged and preserved. Lesion segment 230a has a length and width corresponding or substantially corresponding to the length and width of a sub-array formed by the transducer elements 23 at locations R2C1, R3C1 and R4C1. Lesion segment 230c has a length and width corresponding or substantially corresponding to the length and width of a sub-array formed by transducer elements 23 at locations R2C6, R3C6 and R4C6. The lesion segments 230a and 230c are each solid or continuous along a surface area of rectangular configuration, the lesion segments 230a and 230c having the same length as lesion segment 230b but having a width smaller or less than the width of lesion segment 230b.

An alternative focused ultrasound ablation device according to the present invention is illustrated at 211 in FIG. 8. Focused ultrasound ablation device 211 is similar to focused ultrasound ablation device 11 except that the transducer elements 223 of the focused ultrasound emitting member 212 of device 211 are arranged in rows R that are staggered or offset from one another. In particular, the array formed by transducer elements 223 has a generally rectangular configuration with five rows of transducer elements 223, the transducer elements 223 of rows two and four being vertically offset from or not aligned with the transducer elements of rows one, three and five. In addition, the rows R do not contain an equal number of transducer elements 223, rows one, three and five containing six transducer elements 223 and rows two and four containing five transducer elements 223. As described for focused ultrasound emitting member 12, all or selected ones of the transducer elements 223 can be actuated to emit ultrasound energy.

With the present invention, a single focused ultrasound ablation device can be used to form lesions of various sizes and/or configurations or patterns in anatomical tissue via actuation of selected transducer elements of the focused ultrasound emitting member. In this manner, lesion size and/or configuration can be optimally selected for individual patients. The lesions formed in accordance with the present invention can be continuous or solid, or the lesions can be comprised of disconnected lesion segments. Where lesions comprised of disconnected lesion segments are formed in anatomical tissue, thermal damage to the tissue disposed between, around or surrounding the individual lesion segments can be avoided. Since various sizes and/or configurations or patterns of lesions can be obtained with a singled focused ultrasound ablation device, a single focused ultrasound ablation device can be used to ablate various types of anatomical tissue or structures at various operative sites within or on patients' bodies. The high intensity focused ultrasound ablation device of the present invention can thusly be provided as a standardized device capable of being used in diverse thermal ablation procedures.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A focused ultrasound ablation device for creating a lesion in tissue of a patient comprising:

an ultrasound emitting member having a plurality of individual ultrasound emitting elements spaced from one another, the ultrasound emitting elements being actuatable to emit ultrasound energy a predetermined distance outwardly from an active surface whereby the ultrasound energy is focused within tissue of the patient at separate and distinct locations for each individual ultrasound emitting element to form a lesion, the ultrasound emitting elements being selectively, independently actuatable to emit ultrasound energy and being selectively, independently non-actuatable to not emit ultrasound energy whereby a lesion of selected size and configuration is formed in accordance with the positions of the ultrasound emitting elements selected to be actuated; and a handle coupled to said ultrasound emitting member.

2. The device of claim 1 wherein the ultrasound emitting elements each include a piezoelectric element that emits ultrasound energy in response to electric current selectively supplied thereto.

3. The device of claim 2 wherein the piezoelectric elements are curved to effect focusing of the ultrasound energy a predetermined distance outwardly from the active surface.

4. The device of claim 1 wherein the handle has a sufficient length to position the ultrasound emitting member adjacent tissue in the patient while the handle is maintained external of the patient.

5. The device of claim 1 wherein the handle includes a malleable shaft.

6. The device of claim 1 wherein the handle has a configuration to facilitate grasping by a surgeon or other operator.

7. The device of claim 1 wherein the handle includes one or more controls or switches.

8. The device of claim 7 wherein the one or more controls or switches actuate the emission of ultrasound energy from the ultrasound emitting elements.

9. The focused ultrasound ablation device of claim 1 wherein the ultrasound emitting member further comprises a flexible active surface.

10. The focused ultrasound ablation device of claim 1 wherein the handle is malleable.

11. The focused ultrasound ablation device of claim 1 wherein the plurality of ultrasound emitting elements are arranged in an annular array.

12. The focused ultrasound ablation device of claim 1 wherein the plurality of ultrasound emitting elements are arranged in a linear array.

13. The focused ultrasound ablation device of claim 1 wherein the plurality of ultrasound emitting elements are arranged in a curved linear array.

14. The focused ultrasound ablation device of claim 1 wherein the ultrasound emitting elements emit ultrasound energy at a frequency, wherein the frequency is selectively variable.

15. The focused ultrasound ablation device of claim 1 further comprising a power supply removably coupled to the plurality of individual ultrasound emitting elements and the handle.

16. A focused ultrasound ablation device for creating a lesion within tissue of a patient comprising:
- a handle; and
- an ultrasound emitting member coupled to the handle, the ultrasound emitting member comprising an active face adapted for positioning adjacent an area of tissue, the active face carrying one or more rows of spaced apart ultrasound transducer elements, the ultrasound transducer elements selectively, independently actuatable to emit focused ultrasound energy focused a predetermined distance from the active face and focused at separate and distinct locations for each individual ultrasound transducer element such that the area of tissue adjacent the active face is heated by the focused ultrasound energy to create the lesion within tissue of the patient.

17. The device of claim 16 wherein each of the ultrasound transducer elements includes a piezoelectric element.

18. The device of claim 16 further comprising a power supply coupled to said ultrasound emitting member for generating an electric signal capable of actuating the ultrasound transducer elements to emit focused ultrasound energy.

19. The device of claim 18 further comprising a control unit coupled with the ultrasound emitting member for connecting selected ones of said ultrasound transducer elements with the electrical signal.

20. The focused ultrasound ablation device of claim 18 wherein the power supply is removably coupled to the ultrasound emitting member and the handle.

21. The device of claim 16 wherein the handle includes an elongate shaft.

22. The device of claim 16 wherein the ultrasound emitting elements each include a piezoelectric element that emits ultrasound energy in response to electric current selectively supplied thereto.

23. The device of claim 22 wherein the piezoelectric elements are curved to effect focusing of the ultrasound energy a predetermined distance outwardly from the active surface.

24. The device of claim 16 wherein the handle has a sufficient length to position the ultrasound emitting member adjacent tissue in the patient while the handle is maintained external of the patient.

25. The device of claim 16 wherein the handle includes a malleable shaft.

26. The device of claim 16 wherein the handle has a configuration to facilitate grasping by a surgeon or other operator.

27. The device of claim 16 wherein the handle includes one or more controls or switches.

28. The device of claim 27 wherein the one or more controls or switches are for actuation to emit ultrasound energy from the ultrasound emitting elements.

29. The focused ultrasound ablation device of claim 16 wherein the active surface is flexible.

30. The focused ultrasound ablation device of claim 16 wherein the plurality of ultrasound emitting elements are arranged in an annular array.

31. The focused ultrasound ablation device of claim 16 wherein the plurality of ultrasound emitting elements are arranged in a linear array.

32. The focused ultrasound ablation device of claim 16 wherein the plurality of ultrasound emitting elements are arranged in a curved linear array.

33. The focused ultrasound ablation device of claim 16 wherein the ultrasound emitting elements emit ultrasound energy at a frequency, wherein the frequency is selectively variable.

34. A method of creating an ablation lesion within tissue of a patient comprising:
- grasping a handle coupled to an ultrasound emitting member;
- selecting one or more of a plurality of ultrasound emitting elements, arranged in an array on an active face of the ultrasound emitting member, for actuation to emit ultrasound energy;
- positioning the active face adjacent tissue of the patient;
- actuating the selected one or more ultrasound emitting elements to emit ultrasound energy;
- focusing the ultrasound energy with the selected one or more of the ultrasound emitting elements so that the ultrasound energy is focused a predetermined distance from the active face and focused at separate and distinct locations for each individual ultrasound emitting element; and
- heating the tissue with the focused ultrasound energy to create the ablation lesion.

35. The method of claim 34 wherein the ultrasound emitting elements emit ultrasound energy in response to an electrical signal supplied thereto and the step of actuating includes electrically coupling the selected one or more of the ultrasound emitting elements with an electrical signal source.

36. The method of claim 35 wherein the step of electrically coupling includes electrically coupling the selected one or more of the ultrasound emitting elements with a power supply producing the electrical signal.

37. The focused ultrasound ablation device of claim 36 wherein the power supply is removably coupled to the plurality of individual ultrasound emitting elements and the handle.

38. The method of claim 34 wherein the step of selecting includes selecting a plurality of ultrasound emitting elements to form a continuous lesion.

39. The method of claim 34 wherein the step of selecting includes selecting a plurality of ultrasound emitting elements to form a discontinuous lesion.

40. The method of claim 34 wherein the step of selecting includes selecting a plurality of ultrasound emitting elements to form a lesion comprising a plurality of disconnected lesion segments.

41. The method of claim 34 wherein the handle has a sufficient length for positioning the active face adjacent tissue within the patient while the handle is maintained external of the patient.

42. The method of claim 34 wherein the active face is flexible, and further comprising the step of flexing the active surface.

43. The method of claim 34 wherein the handle is malleable, and further comprising the step of flexing the handle.

44. The focused ultrasound ablation device of claim 34 wherein the plurality of ultrasound emitting elements are arranged in an annular array.

45. The focused ultrasound ablation device of claim 34 wherein the plurality of ultrasound emitting elements are arranged in a linear array.

46. The focused ultrasound ablation device of claim 34 wherein the plurality of ultrasound emitting elements are arranged in a curved linear array.

47. The focused ultrasound ablation device of claim 34 wherein the ultrasound emitting elements emit ultrasound energy at a frequency, wherein the frequency is selectively variable.

48. A focused ultrasound ablation device for creating a lesion in tissue of a patient comprising:

an ultrasound emitting member having a plurality of ultrasound emitting elements, the ultrasound emitting elements being independently actuatable to emit ultrasound energy outwardly from an active surface and being independently non-actuatable to not emit ultrasound energy, whereby the ultrasound energy is focused at separate and distinct locations for each individual ultrasound emitting element;

a controller that selectively, independently actuates the ultrasound emitting elements to emit ultrasound energy, whereby a lesion of selected size and configuration is formed in accordance with the ultrasound emitting elements selected to be actuated.

49. The device of claim 48 wherein the ultrasound emitting elements each include a piezoelectric element that emits ultrasound energy in response to electric current selectively supplied thereto.

50. The device of claim 49 wherein the piezoelectric elements are curved to effect focusing of the ultrasound energy a predetermined distance outwardly from the active surface.

51. The device of claim 48, further comprising a malleable shaft operatively coupled to said ultrasound emitting member.

52. The focused ultrasound ablation device of claim 48 wherein the active surface is flexible in order to conform to a surface of the tissue of the patient.

53. The focused ultrasound ablation device of claim 48 wherein the plurality of ultrasound emitting elements are arranged in an annular array.

54. The focused ultrasound ablation device of claim 48 wherein the plurality of ultrasound emitting elements are arranged in a linear array.

55. The focused ultrasound ablation device of claim 48 wherein the plurality of ultrasound emitting elements are arranged in a curved linear array.

56. The focused ultrasound ablation device of claim 48 wherein the ultrasound emitting elements emit ultrasound energy at a frequency, wherein the frequency is selectively variable.

57. The focused ultrasound ablation device of claim 48 further comprising a power supply removably coupled to the plurality of individual ultrasound emitting elements and the handle.

58. A focused ultrasound ablation device for creating a lesion within tissue of a patient comprising:

an ultrasound emitting member, the ultrasound emitting member comprising an active face adapted for positioning adjacent an area of tissue, the active face carrying one or more rows of spaced apart ultrasound transducer elements, the ultrasound transducer elements selectively, independently actuatable to emit ultrasound energy focused at separate and distinct locations for each individual ultrasound transducer element such that the area of tissue adjacent the active face is heated by the ultrasound energy to create the lesion within tissue of the patient; and a controller operatively coupled to the ultrasound transducer elements, the controller selectively actuating the ultrasound transducer elements.

59. The device of claim 58 wherein each of the ultrasound transducer elements includes a piezoelectric element.

60. The device of claim 58 further comprising a power supply coupled to said ultrasound emitting member for generating an electric signal capable of actuating the ultrasound transducer elements to emit ultrasound energy.

61. The device of claim 60 further comprising a control unit coupled with the ultrasound emitting member for connecting selected ones of said ultrasound transducer elements with the electrical signal.

62. The focused ultrasound ablation device of claim 60 wherein the power supply is removably coupled to the ultrasound emitting member and the handle.

63. The device of claim 58, further comprising an elongate malleable shaft coupled to the ultrasound emitting member.

64. The device of claim 63 wherein the handle has a sufficient length to position the ultrasound emitting member adjacent tissue in the patient.

65. The device of claim 58 wherein the ultrasound emitting elements each include a piezoelectric element that emits ultrasound energy in response to electric current selectively supplied thereto.

66. The device of claim 65 wherein the piezoelectric elements are curved to effect focusing of the ultrasound energy a predetermined distance outwardly from the active surface.

67. The focused ultrasound ablation device of claim 58 wherein the active surface is flexible in order to conform to a surface of the tissue of the patient.

68. The focused ultrasound ablation device of claim 58 wherein the plurality of ultrasound emitting elements are arranged in an annular array.

69. The focused ultrasound ablation device of claim 58 wherein the plurality of ultrasound emitting elements are arranged in a linear array.

70. The focused ultrasound ablation device of claim 58 wherein the plurality of ultrasound emitting elements are arranged in a curved liner array.

71. The focused ultrasound ablation device of claim 58 wherein the ultrasound emitting elements emit ultrasound energy at a frequency, wherein the frequency is selectively variable.

72. A method of creating an ablation lesion within tissue of a patient comprising:

selecting one or more of a plurality of ultrasound emitting elements, arranged in an array on an active face of an ultrasound emitting member, for actuation to emit ultrasound energy;

positioning the active face adjacent tissue of the patient;

actuating the selected one or more ultrasound emitting elements to emit ultrasound energy;

focusing the ultrasound energy with the selected one or more of the ultrasound emitting elements so that the ultrasound energy is focused a predetermined distance from the active face and focused at separate and distinct locations for each individual ultrasound emitting element; and heating the tissue with the focused ultrasound energy to create the ablation lesion.

73. The method of claim 72 wherein the ultrasound emitting elements emit ultrasound energy in response to an electrical signal supplied thereto and the step of actuating includes electrically coupling the selected one or more of the ultrasound emitting elements with an electrical signal source.

74. The method of claim 73 wherein the step of electrically coupling includes electrically coupling the selected one or more of the ultrasound emitting elements with a power supply producing the electrical signal.

75. The focused ultrasound ablation device of claim 74 wherein the power supply is removably coupled to the plurality of individual ultrasound emitting elements.

76. The method of claim 72 wherein the step of selecting includes selecting a plurality of ultrasound emitting elements to form a continuous lesion.

77. The method of claim 72 wherein the step of selecting includes selecting a plurality of ultrasound emitting elements to form a discontinuous lesion.

78. The method of claim 72 wherein the step of selecting includes selecting a plurality of ultrasound emitting elements to form a lesion comprising a plurality of disconnected lesion segments.

79. The method of claim 72, further comprising the step of grasping an elongate malleable shaft coupled to the ultrasound emitting member, wherein the handle has a sufficient length for positioning the active face adjacent tissue within the patient.

80. The method of claim 72 wherein the active face is flexible, and further comprising the step of flexing the active surface.

81. The focused ultrasound ablation device of claim 72 wherein the plurality of ultrasound emitting elements are arranged in an annular array.

82. The focused ultrasound ablation device of claim 72 wherein the plurality of ultrasound emitting elements are arranged in a linear array.

83. The focused ultrasound ablation device of claim 72 wherein the plurality of ultrasound emitting elements are arranged in a curved liner array.

84. The focused ultrasound ablation device of claim 72 wherein the ultrasound emitting elements emit ultrasound energy at a selectively variable frequency, further comprising the step of varying the frequency.

85. A focused ultrasound ablation device for creating a lesion in tissue of a patient comprising:
  a transducer having a plurality of ultrasound emitting elements, the ultrasound emitting elements being independently actuatable to emit ultrasound energy outwardly from an active surface and being independently non-actuatable to not emit ultrasound energy, whereby the ultrasound energy is focused at separate and distinct locations for each individual ultrasound emitting element; and
  a controller that selectively, independently actuates the ultrasound emitting elements to emit ultrasound energy, whereby a lesion of selected size and configuration is formed in accordance with the ultrasound emitting elements selected to be actuated.

86. The device of claim 85 wherein the ultrasound emitting elements each include a piezoelectric element that emits ultrasound energy in response to electric current selectively supplied thereto.

87. The device of claim 86 wherein the piezoelectric elements are curved to effect focusing of the ultrasound energy a predetermined distance outwardly from the active surface.

88. The device of claim 85, further comprising a an elongate malleable shaft coupled to said transducer, wherein the elongate malleable shaft has a sufficient length to position the transducer adjacent tissue in the patient.

89. The focused ultrasound ablation device of claim 85 wherein the transducer is flexible in order to conform with a surface of the tissue of the patient.

90. The focused ultrasound ablation device of claim 85 wherein the plurality of ultrasound emitting elements are arranged in an annular array.

91. The focused ultrasound ablation device of claim 85 wherein the plurality of ultrasound emitting elements are arranged in a linear array.

92. The focused ultrasound ablation device of claim 85 wherein the plurality of ultrasound emitting elements are arranged in a curved liner array.

93. The focused ultrasound ablation device of claim 85 wherein the ultrasound emitting elements emit ultrasound energy at a frequency, wherein the frequency is selectively variable.

94. The focused ultrasound ablation device of claim 85 further comprising a power supply removably coupled to the plurality of individual ultrasound emitting elements.

95. The focused ultrasound ablation device of claim 85 wherein the transducer is flexible and the plurality of ultrasound emitting elements are arranged in a curved linear array in order to conform with a surface of the tissue of the patient.

* * * * *